(12) United States Patent
Parsell et al.

(10) Patent No.: US 10,278,878 B2
(45) Date of Patent: May 7, 2019

(54) EXTREMITY SUPPORT AND IRRIGATION DEVICE AND METHOD OF USE

(71) Applicant: Bone Foam Inc., Plymouth, MN (US)

(72) Inventors: Doug Parsell, Ridgeland, MS (US); Chad Robran, Plymouth, MN (US)

(73) Assignee: BONE FOAM LLC, Plymouth, MN (US)

( * ) Notice: Subject to any disclaimer, the term of this patent is extended or adjusted under 35 U.S.C. 154(b) by 131 days.

(21) Appl. No.: 15/626,469

(22) Filed: Jun. 19, 2017

(65) Prior Publication Data
US 2017/0281446 A1  Oct. 5, 2017

Related U.S. Application Data

(63) Continuation-in-part of application No. 13/766,063, filed on Feb. 13, 2013.
(Continued)

(51) Int. Cl.
*A61G 15/00* (2006.01)
*A61G 13/10* (2006.01)
(Continued)

(52) U.S. Cl.
CPC ........ *A61G 13/102* (2013.01); *A61B 17/3203* (2013.01); *A61B 46/27* (2016.02);
(Continued)

(58) Field of Classification Search
CPC .............. A61H 35/00; A61H 2035/004; A61H 35/006; A61M 1/008; A61M 1/00; A61M 2205/75; A61M 3/0266; A61M 3/02; A61M 1/0058; A61M 1/0023; A61B 46/00; A61B 46/10; A61B 46/20; A61B 2046/201; A61B 46/23; A61B 2046/236; A61B 46/27;
(Continued)

(56) References Cited

U.S. PATENT DOCUMENTS 3,762,404 A  10/1973 Sakita
3,873,081 A   3/1975 Smith
(Continued)

OTHER PUBLICATIONS

ISR and Written Opinion for PCT Application No. PCT/US2014/014913 dated Apr. 25, 2014.

*Primary Examiner* — Victoria J Hicks
(74) *Attorney, Agent, or Firm* — Workman Nydegger (57) ABSTRACT

An apparatus for supporting an extremity during tissue irrigation and debridement and containing and capturing fluid and tissue debris resulting therefrom includes an extremity-supporting base and barrier shroud. The apparatus can be used to control drainage of fluid and tissue debris during irrigation and debridement. The apparatus supports and encloses a patient extremity, such as an arm or a leg. The base has a length, proximal end (i.e., nearest the patient's body), and distal end (i.e., farthest from the patient's body). The base may comprise an open-cell foam that is non-collapsible to provide a support surface with a fixed length. The shroud has a top portion, bottom portion, and shroud drainage opening. The shroud can be selectively moveable between a first position in which the support surface is unobstructed to facilitate placement of an extremity thereon and a second position in the shroud at least partially encloses the extremity.

18 Claims, 7 Drawing Sheets

Related U.S. Application Data (60) Provisional application No. 61/633,464, filed on Feb. 13, 2012.

(51) Int. Cl.
*A61B 17/3203* (2006.01)
*A61M 3/02* (2006.01)
*A61G 13/12* (2006.01)
*A61M 1/00* (2006.01)
*A61B 46/27* (2016.01)
*A61B 46/20* (2016.01)

(52) U.S. Cl.
CPC ..... *A61G 13/1235* (2013.01); *A61G 13/1245* (2013.01); *A61M 1/0088* (2013.01); *A61M 3/0287* (2013.01); *A61B 2046/201* (2016.02); *A61M 1/0056* (2013.01)

(58) Field of Classification Search
CPC .. A61B 90/40; A61G 13/102; A61G 13/1235; A61G 13/1245; A61G 13/125; A61G 13/126; A61G 13/128; A61G 13/1285; A61G 13/00; A61G 13/12; A61G 13/1205; A61G 13/124; A61G 13/10; A61G 7/047
See application file for complete search history.

(56) References Cited

U.S. PATENT DOCUMENTS

| | | | | |
|---|---|---|---|---|
| 4,136,858 | A | 1/1979 | Peterson | |
| 4,194,601 | A | 3/1980 | Yellin | |
| 4,218,792 | A | 8/1980 | Kogan | |
| 4,481,943 | A | 11/1984 | Michalson | |
| 4,620,698 | A | 11/1986 | Reed | |
| 4,681,309 | A | 7/1987 | Lechner | |
| 4,742,981 | A | 5/1988 | Converse | |
| 4,745,647 | A | 5/1988 | Goodwin | |
| 4,836,523 | A | 6/1989 | Englander | |
| 4,863,788 | A | 9/1989 | Bellairs | |
| 4,974,604 | A | 12/1990 | Morris | |
| 5,014,375 | A | 5/1991 | Coonrad | |
| 5,016,268 | A | 5/1991 | Lotman | |
| 5,125,123 | A | 6/1992 | Engle | |
| 5,178,162 | A | 1/1993 | Bose | |
| 5,289,828 | A | 3/1994 | Toth | |
| 5,312,385 | A | 5/1994 | Greco | |
| 5,316,541 | A | 5/1994 | Fischer | |
| 5,349,965 | A | * 9/1994 | McCarver | A61G 13/102 128/846 |
| 5,369,825 | A | 12/1994 | Reesby | |
| 5,381,562 | A | * 1/1995 | Holloway | A45D 19/06 4/516 |
| 5,437,602 | A | 8/1995 | Polyakov et al. | |
| 5,439,008 | A | 8/1995 | Bowman | |
| 5,462,551 | A | 10/1995 | Bailey | |
| 5,609,163 | A | 3/1997 | Beard | |
| 5,645,079 | A | 7/1997 | Zahiri | |
| 5,754,997 | A | 5/1998 | Lüssi | |
| 5,775,334 | A | 7/1998 | Lamb | |
| 5,809,597 | A | 9/1998 | Shaw | |
| 5,819,743 | A | 10/1998 | McMillan | |
| 5,836,309 | A | * 11/1998 | Webb | A61B 50/33 128/845 |
| 5,906,205 | A | 5/1999 | Hiebert | |
| 6,032,669 | A | 3/2000 | Klein | |
| 6,402,724 | B1 | 6/2002 | Smith et al. | |
| 6,405,389 | B1 | * 6/2002 | Harty | A47K 3/062 4/621 |
| 6,553,995 | B1 | 4/2003 | Cole et al. | |
| 7,678,092 | B2 | 3/2010 | Matloub et al. | |
| 8,726,907 | B2 | 5/2014 | Strauch et al. | |
| 2004/0225265 | A1 | 11/2004 | Tapadiya | |
| 2011/0297164 | A1 | * 12/2011 | Strauch | A61B 19/088 128/849 |
| 2013/0211425 | A1 | 8/2013 | Parsell | |

\* cited by examiner

EXTREMITY SUPPORT AND IRRIGATION DEVICE AND METHOD OF USE

CROSS REFERENCE TO RELATED APPLICATIONS

The Application is a continuation-in-part of U.S. application Ser. No. 13/766,063, filed Feb. 13, 2013, which claims the benefit of U.S. Provisional Application No. 61/633,464, filed Feb. 13, 2012, the disclosures of which are incorporated herein in their entirety.

BACKGROUND OF THE INVENTION

1. The Field of the Invention

The present invention relates to devices and methods for use in removing biological debris from patient extremities. More specifically, the present invention relates to medical irrigation devices and methods for containing the fluid and solid biological debris ejected as a result of debridement using high-pressure jetted fluid.

2. Background and Relevant Art

Within the medical arts, it is common practice to remove infected and/or necrotic tissues to allow for increased healing rates and to decrease infection risk. The clinical procedure for the above mentioned action is termed wound debridement. A common component of the debridement process is copious fluid irrigation of the targeted tissue areas. The fluids used are typically sterile saline but fluid with additional antimicrobial agents may also be utilized.

In general, known techniques for tissue debridement include surgical, chemical, mechanical, and autolytic. Surgical debridement techniques include conventional surgical techniques, involving the use of sharp medical instruments, and hydrosurgical techniques, involving the use of a high-pressure stream or spray of jetted fluid.

In hydrosurgical debridement, infected and/or necrotic tissue (i.e., tissue that is dead, burned, diseased, infected, etc.), is ablated using a stream or spray of water, saline, or other fluid directed under very high pressure at the tissue to be removed. Because large amounts of fluid are required, and because the high pressure of the fluid against the targeted necrotic tissue can results in uncontrolled emission of fluid as well as the ablated pieces of infected and/or necrotic tissue, hydrosurgical debridement can be unsanitary and messy.

Uncontrolled tissue and fluid emission associated with hydrosurgical debridement can create problems for medical staff, such as contamination of equipment, clothing, face shields or eye protection. In addition, hydrosurgical debridement procedures can require the complete turnover and re-sterilization of some or all of equipment in the operating room, as well as a thorough disinfection and sterilization of every surface in the operating room. Turnover, sterilization and disinfection procedures are labor-intensive, time-consuming, and expensive.

As such, there exists a need for extremity supporting structures that facilitate the effective and convenient deployment of the irrigation and debridement process.

BRIEF SUMMARY

Disclosed herein are embodiments of apparatus for supporting an extremity during tissue debridement and capturing fluid and tissue resulting from tissue debridement and methods of debriding tissue of an extremity and capturing fluid and tissue resulting from tissue debridement. The apparatus and methods can provide improved sanitary conditions for a patient and medical personnel involved in a tissue debridement procedure, as well as a cleaner environment in the medical facility.

According to one embodiment, an apparatus for supporting an extremity during tissue debridement and capturing fluid and tissue includes an extremity-supporting base with a support surface configured to support an extremity of a patient during tissue debridement. The base can have a proximal end positioned nearest a patient's body during use and a distal end opposite the proximal end. A barrier shroud can be positionable so as to at least partially enclose an extremity placed on the extremity-supporting base. A drainage passageway can be provided that is in fluid communication with the extremity-supporting base and barrier shroud, which provides controlled drainage of fluid and tissue from the extremity-supporting base and barrier shroud during tissue debridement.

The extremity-supporting base may include a trough, such as a concave trough, for cradling an extremity. The trough may have a trough bottom and a side wall on either side of the trough bottom. The extremity-supporting base may be downwardly angled toward the drainage passageway to facilitate movement of fluid and tissue toward the drainage passageway during tissue debridement. According to one embodiment, the drainage passageway is positioned at or near the distal end of the base to facilitate movement of fluid and tissue away from the patient's body during tissue debridement. The drainage passageway can be provided by a hole through the base and/or barrier shroud. A drainage tube may be attached to the drainage passageway to facilitate drainage of fluid and tissue into a receiving vessel. Drainage may be gravitational or aspiration assisted.

According to one embodiment, the barrier shroud comprises a flexible sheet material, such as a water-proof polymer. One or more braces that cooperate with the flexible barrier shroud may advantageously maintain the barrier shroud in a desired elevated configuration above the extremity-supporting base and relative to an extremity during debridement (e.g., to provide space between the shroud and extremity). The barrier shroud may include one or more fasteners that permit selective opening and closing of the barrier shroud relative to an extremity placed on the extremity-supporting base. The barrier shroud may include an opening in an upper region that permits access to the extremity by a debridement instrument, such as a high pressure irrigation device.

According to one embodiment, the extremity-supporting base may be formed from an open-cell foam material (e.g., flexible polyurethane foam). A flexible, fluid-impermeable coating may be positioned over at least a portion of the open-cell foam material to provide additional sterility and ease of cleaning.

According to another embodiment, a method of debriding tissue of an extremity and capturing fluid and tissue resulting from tissue debridement includes: (1) placing an extremity of a patient on an extremity-supporting base (i.e., a support surface provided by the top side of the base); (2) at least partially enclosing said extremity with a barrier shroud; and (3) debriding a portion of said extremity using a high-pressure fluid, (4) the base and barrier shroud providing a containment space for substantially containing fluid and tissue resulting from tissue debridement and controlling drainage of said fluid and tissue. The method may include gravitational and/or aspiration assisted drainage of fluid and tissue through a drainage hose in fluid communication with the barrier shroud and base.

This Brief Summary is provided to introduce in a simplified form a selection of concepts that are further described below in the Detailed Description. This Brief Summary is not intended to identify key or essential features of the claimed subject matter, nor is it intended to be used as an aid in determining the scope of the claimed subject matter. Additional features and advantages of the invention will be set forth in the description which follows, and in part will be evident to persons of ordinary skill in the art from the description and appended claims, or may be learned by such persons through the practice of the invention.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the FIGS. are not necessarily drawn to scale, and that elements of similar structure or function are generally represented by like reference numerals for illustrative purposes throughout the figures. These drawings depict only certain embodiments of the invention and are not therefore to be considered to be limiting of its scope.

DETAILED DESCRIPTION

The following are example embodiments of apparatus for supporting an extremity during tissue debridement and capturing fluid and tissue resulting from tissue debridement and methods of debriding tissue of an extremity and capturing fluid and tissue resulting from tissue debridement. According to one embodiment, an extremity supporting medical irrigation ramp (or apparatus for supporting an extremity during tissue debridement and capturing fluid and tissue resulting from tissue debridement) is composed of two elements: an extremity-supporting, fluid-channeling element (or extremity-supporting base) and a sterile, barrier element (or barrier shroud). In one embodiment, the extremity-supporting base may be constructed from open-cell foam material at least partially covered with a fluid impermeable, flexible exterior coating. The exterior coating may comprise a polymeric, non-latex composition. Alternatively, or in addition, a portion of the barrier shroud can cover the top side of the support base and provide a water-resistant barrier between the support surface and an extremity placed thereon.

As illustrated in the drawings and described in more detail below, an implementation of the invention provides an apparatus for supporting and at least partially enclosing an extremity of a patient during tissue irrigation and debridement, wherein the apparatus comprises: (1) a support base extending between a proximal end and a distal end and having a bottom side and a top side providing a support surface for placement and support of an extremity thereon; and (2) a barrier selectively moveable between a first configuration, in which the support surface is vertically unobstructed to permit an extremity to be lowered from a position above and downwardly onto the support surface, and a second configuration, in which the barrier is positioned over the support surface in order to at least partially cover an extremity on the support surface.

In some embodiments, the support base comprises a rigid or semi-rigid material (e.g., open-cell polymer foam, such as polyurethane foam) that is non-collapsible so as to have a fixed length from the proximal end to the distal end. For example, at least a portion of the support base may comprise a rigid or semi-rigid material that is non-collapsible so that the support surface provides a continuous surface of fixed length and width that supports at least a majority of the length of an extremity, such as a human leg or arm. In some embodiments, the bottom side of the support base is generally flat and the top side is concave so that the support surface forms or is provided by a trough of fixed length, fixed width, and fixed depth. In some embodiments, the or semi-rigid material of the support base has a thickness at the proximal end that is greater than a thickness at the distal so that the support surface or trough slopes downwardly and facilitates drainage of irrigation fluid toward the distal end.

In some embodiments, the barrier is provided by a flexible polymer sheet material, wherein (1) a first portion of the barrier (polymer sheet material is positionable over the support surface to provide a water-resistant barrier between the continuous support surface and an extremity placed thereon and (2) a second portion of the barrier (polymer sheet material) is selectively positionable to provide the first and second configurations of the barrier. One or more fasteners may be provided, such as Velcro® or adhesive tape, that can be unfastened when the second portion of the barrier (polymer sheet material) is in the first open configuration that permits placement of an extremity onto the support surface and selectively fastened when the second portion of the barrier (polymer sheet material) is in the second configuration covering the extremity to provide a containment space to contain water and debris and prevent it from splashing onto the practitioner(s) while performing an irrigation and debridement procedure on the extremity. As illustrated in FIGS. 3-7, the barrier can include a third portion (polymer sheet material) positionable beneath the bottom side of the support base so that the first and third barrier portions form an enclosure having an open proximal end and a closed distal end and that is configured to enclose the support base, including the top and bottom sides of the support base, during use.

As further illustrated in the drawings and described in more detail below, an implementation of the invention provides an apparatus for supporting and at least partially enclosing an extremity of a patient during tissue irrigation, comprising: (1) a support base comprising a rigid or semi-rigid material extending between a proximal end and a distal end and having a bottom side and a top side providing a support surface of fixed longitudinal length for placement and mechanical support of an extremity thereon; and (2) a barrier comprising a flexible sheet having a first sheet portion positionable on the support surface and a second sheet portion selectively positionable between a first configuration, in which the first sheet portion is vertically unobstructed to permit an extremity to be lowered from a position above and downwardly onto the first sheet portion, and a second configuration, in which the second sheet portion is positioned over the first sheet portion in order to at least partially cover an extremity placed on the first sheet portion and mechanically supported by the support surface. As shown in FIGS. 3-7, the flexible sheet can include a third sheet portion positionable beneath the bottom side of the support base so that the first and third sheet portions form a bag or sleeve structure having an open proximal end and a closed distal end and that is configured to enclose the support base, including the top and bottom sides of the support base, during use.

As further illustrated in the drawings and described in more detail below, an implementation of the invention provides an apparatus for supporting and at least partially enclosing an extremity of a patient during tissue irrigation, comprising: (1) a support base comprising a rigid or semi-rigid material extending between a proximal end and a distal end and having a bottom side that is generally flat and a top side that is concave and forms a trough of fixed length, fixed width, and fixed depth that provides a support surface for placement and mechanical support of an extremity thereon; and (2) a barrier selectively moveable between a first configuration, in which the trough is vertically unobstructed to permit an extremity to be lowered from a position above and downwardly onto the support surface, and a second configuration, in which the barrier is positioned over the trough in order to at least partially cover an extremity on the support surface.

The terms "rigid" and "semi-rigid" shall have their ordinary meaning. For example, it is known that a flexible open-cell polymer foam material can be a semi-rigid material, even if flexible to provide a cushion, because it can have a defined structure of fixed length, fixed width, and even fixed thickness. Depending on the flexibility and resiliency (or spring-back property) of the open-cell polymer foam material the and weight of an object placed thereon, an open-cell polymer structure may or may not become compressed when an object (such as an extremity) is placed thereon; however, when the object is removed, the open-cell foam material will usually rebound and assume its original shape and native thickness.

When an extremity, such as a leg or arm, is placed onto the support apparatus the support surface can "support" the extremity whether or not there is direct contact of the extremity and support surface (e.g., whether or not there is a flexible polymer sheet interposed between the extremity and the support surface). It shall be understood that the extremity can be "placed onto" and be "supported by" the support surface whether or not they directly touch each other or there is a water-resistant barrier between them.

The extremity-supporting base may include a concave surface that supports the patient's extremity (e.g., arm or leg). The concavity of the extremity-supporting element can function to channel fluids applied during the debridement procedure, and also tissue removed during debridement, toward a distal end of the device. The extremity-supporting base may further include a downward slope, which slopes downward toward a distal end of the extremity-supporting base. In one embodiment, a dam feature at a distal end of the apparatus allows for pooling of applied fluids and removed tissues. A drainage hole at or near the distal end allows for the continuous removal/evacuation of fluids and tissue. The dam might form part of the extremity-supporting base and/or it may be part of the barrier shroud.

For each individual debridement case (i.e., each new patient extremity), a new sterile, barrier element or shroud may be used by placing it between the patient's extremity and the extremity-supporting base. In this way, the extremity-supporting base can be kept sterile and re-used if desirable while the barrier shroud is a single-use, disposable feature. Alternatively, the base may itself be disposable. The barrier shroud can be a smooth plastic sheet that easily conforms to the concave shape of the extremity-supporting base and is advantageously of adequate size to cover all potential patient extremity-contacting surfaces of the extremity-supporting base.

According to one embodiment, the barrier element may include a drainage hole and an integrated, semi-rigid drainage tube that is of a diameter to slide into a drainage hole at the distal extent of the extremity-supporting base (when included). The drainage tube can be of sufficient length to extend significantly beyond the bottom surface of the extremity-supporting base, when fully engaged. Alternatively, a drainage tube can be attached to the drainage hole of the barrier element when positioned beyond a distal end of the extremity-supporting element. The drainage tube allows for fluids applied during the debridement procedure to exit the device via gravity-assisted, fluid movement into a receiving vessel or, alternatively, via suction assisted evacuation of fluids.

To further capture fluid droplets that may possess an upwards trajectory during the debridement procedure, the sterile covering element or shroud may comprise a "greenhouse" structure (e.g., by means of hoops or braces that hold the barrier shroud in a desired configuration during use). This feature can attach at the lateral edge of the device and arch over the extremity. The "greenhouse" structure can be made from clear plastic to allow for adequate visualization of the debridement field. Right and left side slits may run along the length of the "greenhouse" structure, so as to allow for insertion of a tip of an irrigation device through the plastic barrier and direct access to the debridement site.

The top portion of the barrier shroud may include an opening formed therein to allow a hydrosurgical debridement device to access the debridement site of the extremity. The top portion and bottom portion may be joined together around the edges in either a permanent manner or in a manner designed to allow the shroud to be opened and closed (e.g., like a sleeping bag). The top portion and bottom portion of the shroud may include fasteners such as snaps, Velcro® (hook and loop), zippers, hooks, clasps, adhesive tape, or other fastening elements known in the art which can allow the shroud to be selectively opened and closed.

Figure 1A:
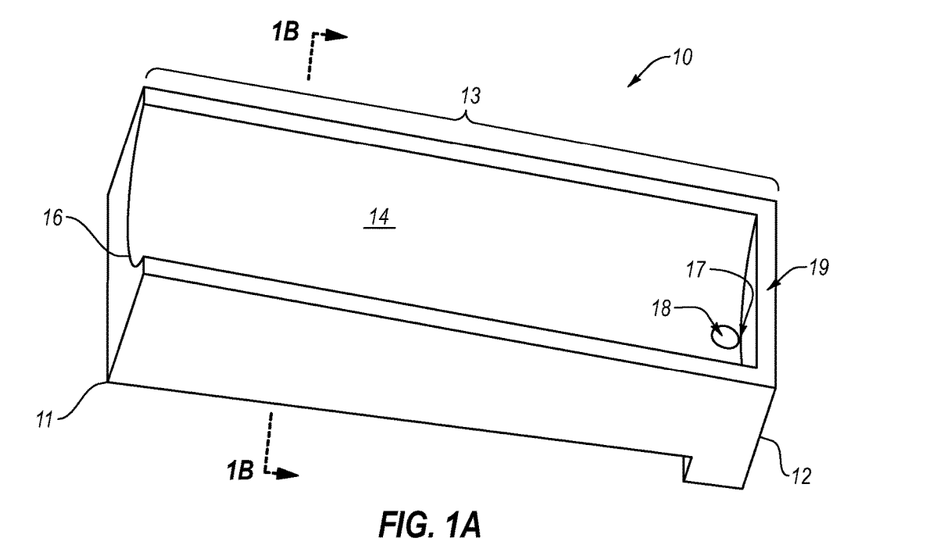
FIG. 1A illustrates an example embodiment of an extremity-supporting base having a downward sloping concave trough with a dam and drainage opening at a distal end.

Referring now to FIG. 1A, an embodiment of an extremity-supporting base 10 is shown. Base 10 has a proximal end 11 and a distal end 12 defining a length 13 between proximal end 11 and distal end 12. Proximal end 11 is typically positioned nearest to the patient's body (e.g., torso in the case of a leg or shoulder in the case of an arm). Distal end 12 is typically the end farthest away from the patient's body.

Figure 1B:
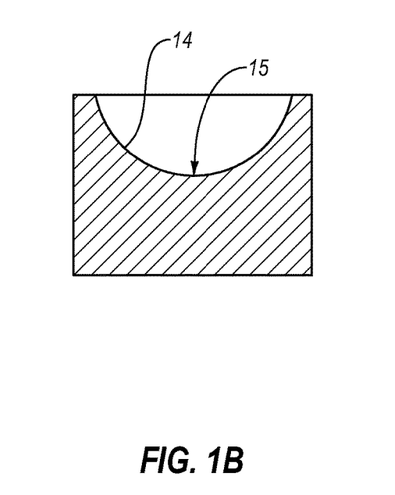
FIG. 1B is a transverse cross-sectional view of FIG. 1A.

Base 10 is configured for use as a support for a patient extremity, such as an arm or a leg, which can be further enclosed within a shroud, discussed below, during the process of hydrosurgical wound debridement. According to one embodiment, support base 10 can have a concave support surface to help cradle and hold a patient extremity in a desired orientation, and which can direct fluid and tissue debris associated with hydrosurgical debridement toward the lowest point of a downwardly sloping support surface. Base 10 may therefore be constructed such that a trough 14 having a concave shape (and providing a support surface) extends along part or all of the length 13 of base 10. Trough 14 as illustrated includes a trough bottom 15 that also runs along part or all of the length 13 of base 10. Trough 14 and trough bottom 15 are more particularly illustrated in FIG. 1B, which is a cross-sectional view of base 10 as seen from proximal end 11.

To control runoff of fluid and tissue debris associated with a debridement procedure, trough 14 can be sloped downward along the base length 13 from a high point 16 at proximal end 11 (where base 10 has greater height or vertical thickness) to low point 17 at distal end 12 (where base 10 has lesser height or vertical thickness). In the illustrated embodiment, positioned at or near the low point 17 is a base drainage opening or passageway 18. A base dam 19 is positioned at distal end 12 in close proximity to base drainage opening 18 such that excess fluid and tissue debris associated with debridement can build-up in the area adjacent to base drainage opening 18, which facilitates controlled drainage of such fluid and tissue debris through passageway or hole 18. Drainage can be by gravity alone or assisted by applied vacuum suction.

In an alternative embodiment (not shown), the trough bottom may include more than one high point and either side of a low point. The multiple high points and trough bottom low point may be arranged such that a trough bottom low point is located at or near the center of the base to promote drainage through a passageway at this location. Alternatively, the trough bottom may include a high point in the center and low points at the proximal and distal ends.

Base 10 may be made of open-cell foam and may have a coating thereof that is fluid-impermeable and flexible. The coating on base 10 may be formed of a polymeric, non-latex composition. The open-cell foam can provide a semi-rigid, non-collapsible structure that can maintain a fixed length (i.e., length 13) before and during use. The open-cell foam (e.g., polyurethane foam) can be lightweight yet can maintain a predetermined shape and size to facilitate ease of placement of support base 10 on a patient support platform (e.g., bed or operating table) and ease of placement of an extremity thereon without fear of unwanted or unintended collapse (which could result in severe harm to a badly damaged extremity).

Figure 2A:
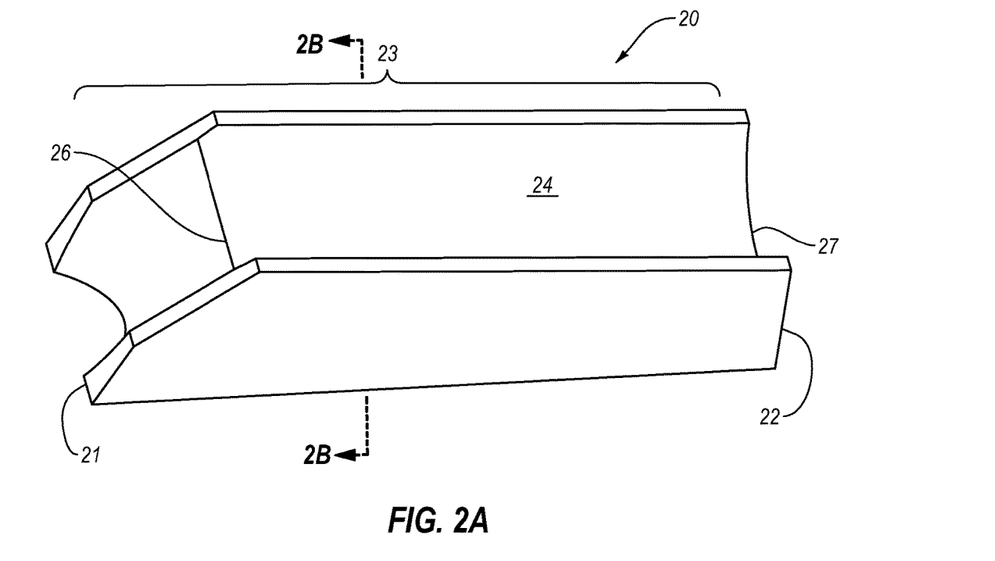
FIG. 2A illustrates an alternative embodiment of an extremity-supporting base having a downward sloping concave trough and being open at a distal end.
Figure 2B:
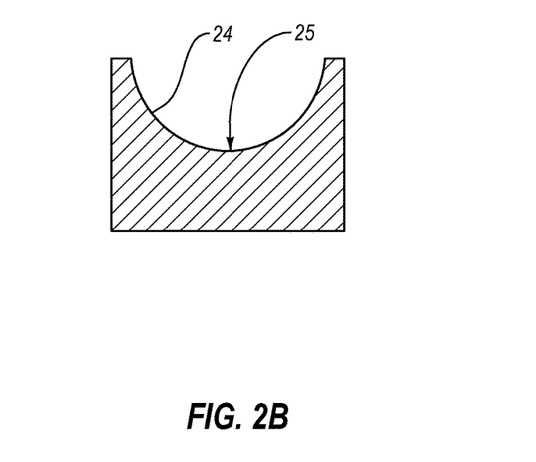
FIG. 2B is a transverse cross-sectional view of FIG. 2A.

Referring now to FIG. 2A, another embodiment of an extremity-supporting base 20 is illustrated. Some features of base 20 are the same as those of base 10 with two primary exceptions: base 20 has neither a base dam nor a base drainage opening (such as elements 18 and 19, respectively, shown in FIG. 1A). Otherwise, support base 20 includes a proximal end 21, a distal end 22, a length 23, a trough 24, a trough bottom 25 (shown in FIG. 2B, which is a cross-sectional view of base 20 viewed from distal end 22), a trough bottom high point 26 (where base 20 has greater height or vertical thickness), and a trough bottom low point 27 (where base 20 has greater height or vertical thickness). Thus, trough 24 slopes downwardly toward distal end 22.

Like base 10, base 20 is designed for use as a support for a patient extremity, such as an arm or a leg, during the process of tissue debridement. Because base 20 does not have a base dam or a base drainage opening, an embodiment of a barrier shroud (discussed below) that cooperates with base 20 may be different than the shroud embodiment designed to cooperate with base 10. Specifically, the shroud drainage opening does not align with a base drainage opening when using base 20 because base 20 has no base drainage opening. In one embodiment, base 20 may be used with and support a barrier shroud having a shroud dam and a shroud drainage opening that are positioned beyond distal end 22 of base 20, as will be discussed in more detail below.

Like base 10, base 20 may be made of open-cell foam and may have a coating that is fluid-impermeable and flexible. The coating on base 20 may be formed of a polymeric, non-latex composition. The open-cell foam can provide a semi-rigid, non-collapsible structure that can maintain a fixed length (i.e., length 23) before and during use to facilitate placement of base 20 on a patient support platform and ease of placement of an extremity thereon without fear of unwanted or unintended collapse Although not depicted in the drawings, base 10 may operate together with a shroud that has a shroud drainage opening and a drainage hose that cooperate with base drainage opening 18 of base 10 such that the shroud includes a drainage opening which substantially lines up over base drainage opening 18 and a drainage hose that fits down and through base drainage opening 18 and extends beyond an underside of base 10.

Figure 3:
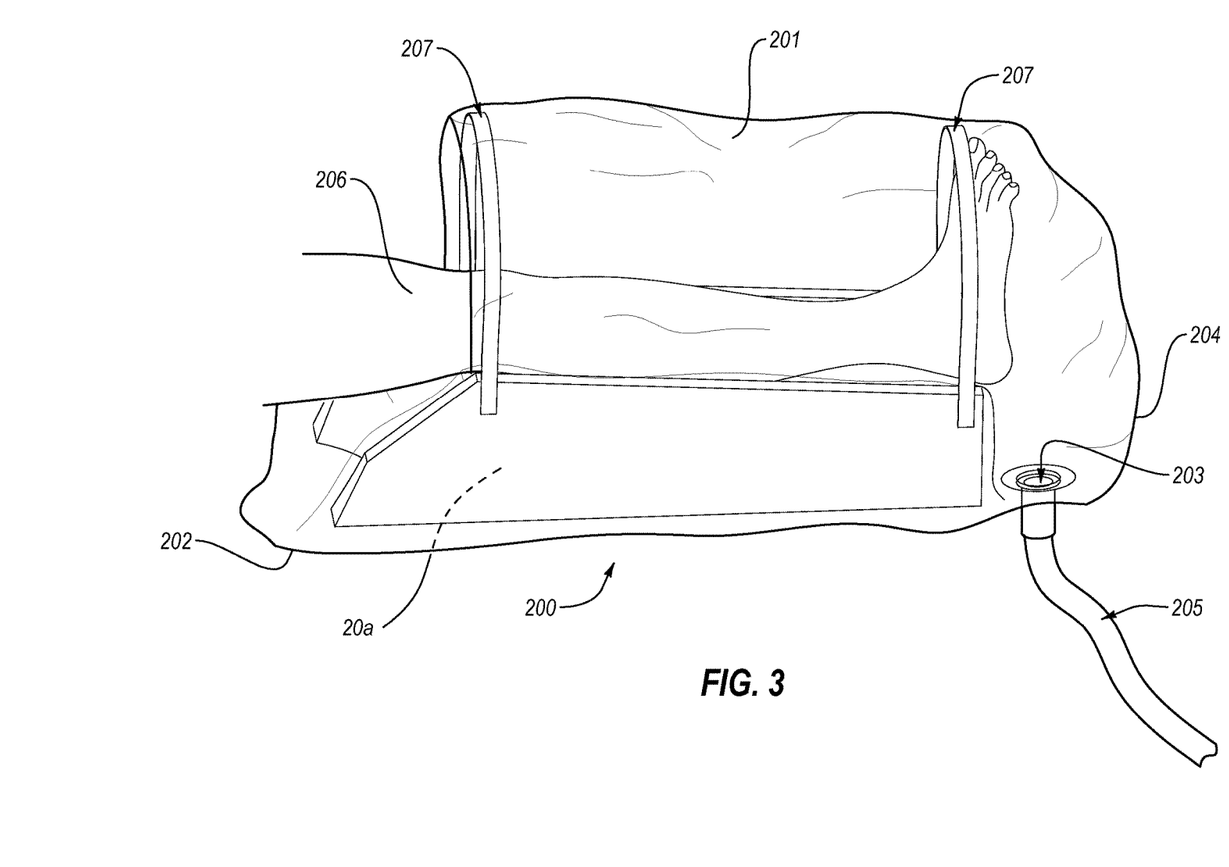
FIG. 3 illustrates an example embodiment of an apparatus for supporting an extremity during tissue debridement and capturing fluid and tissue, which includes a base supporting an extremity (i.e., leg) and a flexible barrier shroud partially enclosing the extremity.

FIG. 3 illustrates an extremity-supporting base 20a similar to base 20 in cooperation with an embodiment of a barrier shroud 200. This embodiment of shroud 200 as shown has a top portion 201, a bottom portion 202, and a shroud drainage opening 203. A shroud dam 204 is formed by a raised or vertical portion just beyond shroud drainage opening 203 interconnecting top portion 201 and bottom portion 202. Shroud drainage opening 203 is attached to a drainage hose 205 that extends down and leads away from shroud 200. Shroud dam 204 is positioned beyond and below a distal end of the base in close proximity to shroud drainage opening 203 such that the excess fluid and tissue debris associated with tissue debridement may pool in an area of shroud 200 beyond and below the distal end of the base. Fluid and tissue may exit shroud drainage opening 203 with the aid of gravity and/or applied vacuum suction.

The availability of vacuum suction may alternatively permit shroud drainage opening 203 to be alternatively located in other regions of the shroud 200, such as in dam 24 or even top portion 201 of shroud 200 if top and bottom portions 201, 202 of shroud 200 are sealed at all points except the opening adjacent to the proximal end of the base.

One purpose of barrier shroud 200 is to contain fluid and removed tissue that may tend to spatter or be emitted from patient extremity 206 during the debridement process. Consistent with this purpose, the material for shroud 200 is advantageously fluid-impermeable or fluid-resistant. However, since shroud 200 is intended only for a single use and need not endure repeated exposure to fluid, materials that are not strictly fluid-resistant or fluid-impermeable may suffice.

In use, shroud 200 is positioned over patient extremity 206 such that bottom portion 202 of shroud 200 lies beneath extremity 206 but above the support surface of base 20, which supports the shroud-encased patient extremity 206. Top portion 201 of shroud 200 further includes one or a plurality of braces 207 operatively associated with top portion 201, although two braces 207 are shown in this illustrated embodiment. One purpose of brace 207 is to suspend top portion 201 over patient extremity 206 such that top portion 201 does not come into substantial contact with patient extremity 206. Another purpose of brace 207 is to provide the surgeon and medical staff with sufficient working space above patient extremity 206 but below top portion 201 so as to allow for the effective carrying out of a hydrosurgical debridement procedure.

The material used for brace 207 and the mechanism for operatively relating brace 207 with top portion 201 may be selected from any of a number of materials and methods consistent with accomplishing these purposes. Brace 207 may be operatively associated with top portion 201 in any of a number of conventional ways, including, but not limited to, being slidably positioned in a slot formed in top portion 201, fixedly attached to top portion 201 with adhesive, or integrally formed into the material of top portion 201 during manufacture. Brace 207 may be of fixed shape, such as the arcuate shape illustrated in FIG. 3, or may be of a deformable material, such as a soft metal, that can be manipulated into a desired shape.

Figure 4:
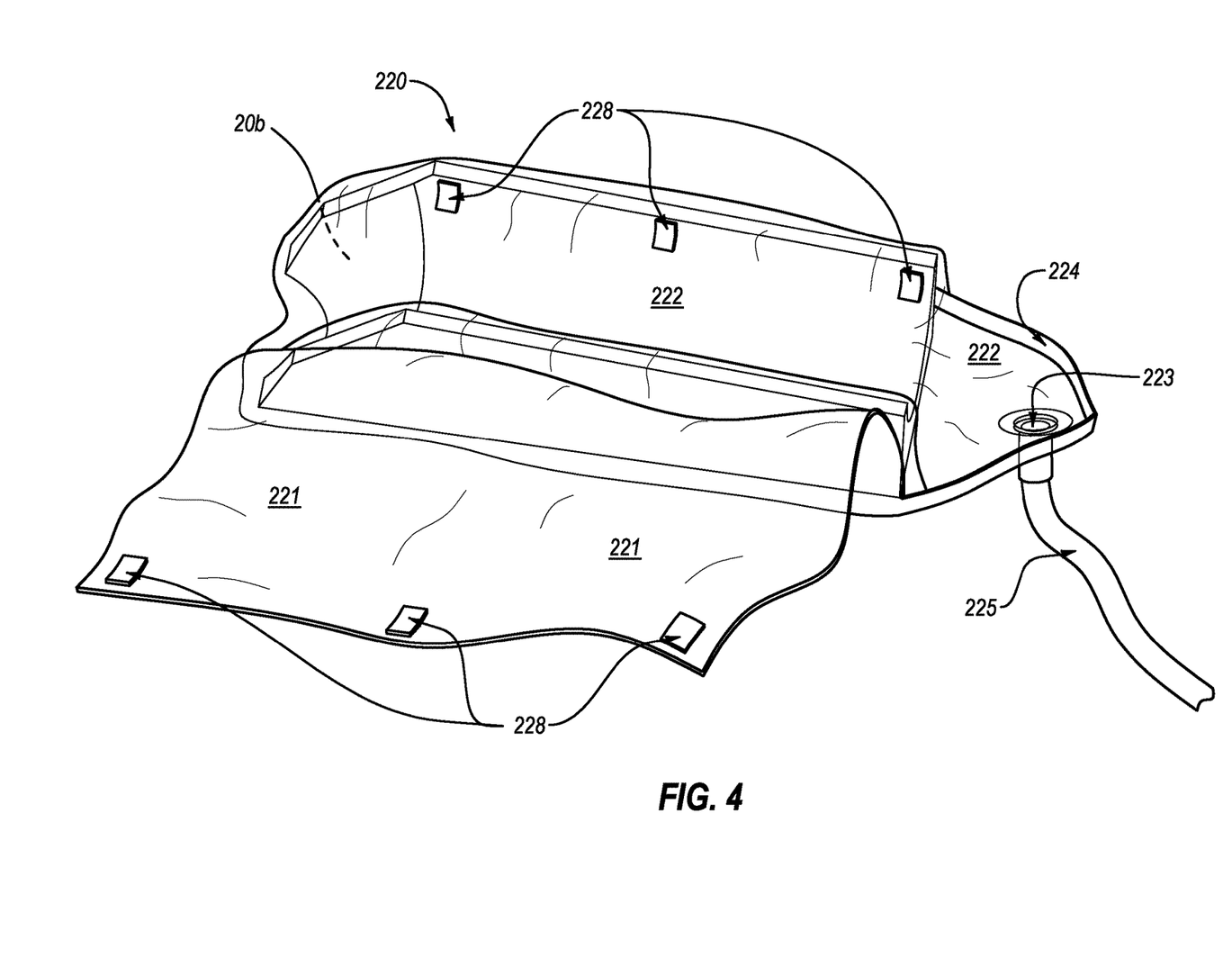
FIG. 4 illustrates another embodiment of an apparatus for supporting an extremity during tissue debridement and capturing fluid and tissue, which includes an extremity-supporting base, a flexible barrier shroud with fasteners that permit selective fastening and unfastening of the shroud during placement and removal of an extremity on the base, and a drainage hole and tube at a distal end of the barrier shroud.

Shroud 200 of FIG. 3 may be formed in a manner similar to that shown in FIG. 4 such that top portion 201 opens like a flap, or the top part of a sleeping bag, wherein top portion 201 is permanently joined to bottom portion 202 along one edge of shroud 200 (adjacent the length 23 of the base 20) and is attachable to bottom portion 202 along the opposite edge using known fastening devices such as snaps, Velcro® (hook and loop), buttons, clasps, hooks, adhesive tape, or zippers.

Top portion 201 and bottom portion 202 of shroud 200 may be joined in the manner shown in FIG. 3, that is, permanently joined along both opposing side edges and may or may not be permanently joined along the bottom edge, adjacent distal end of the base 20.

Figure 7:
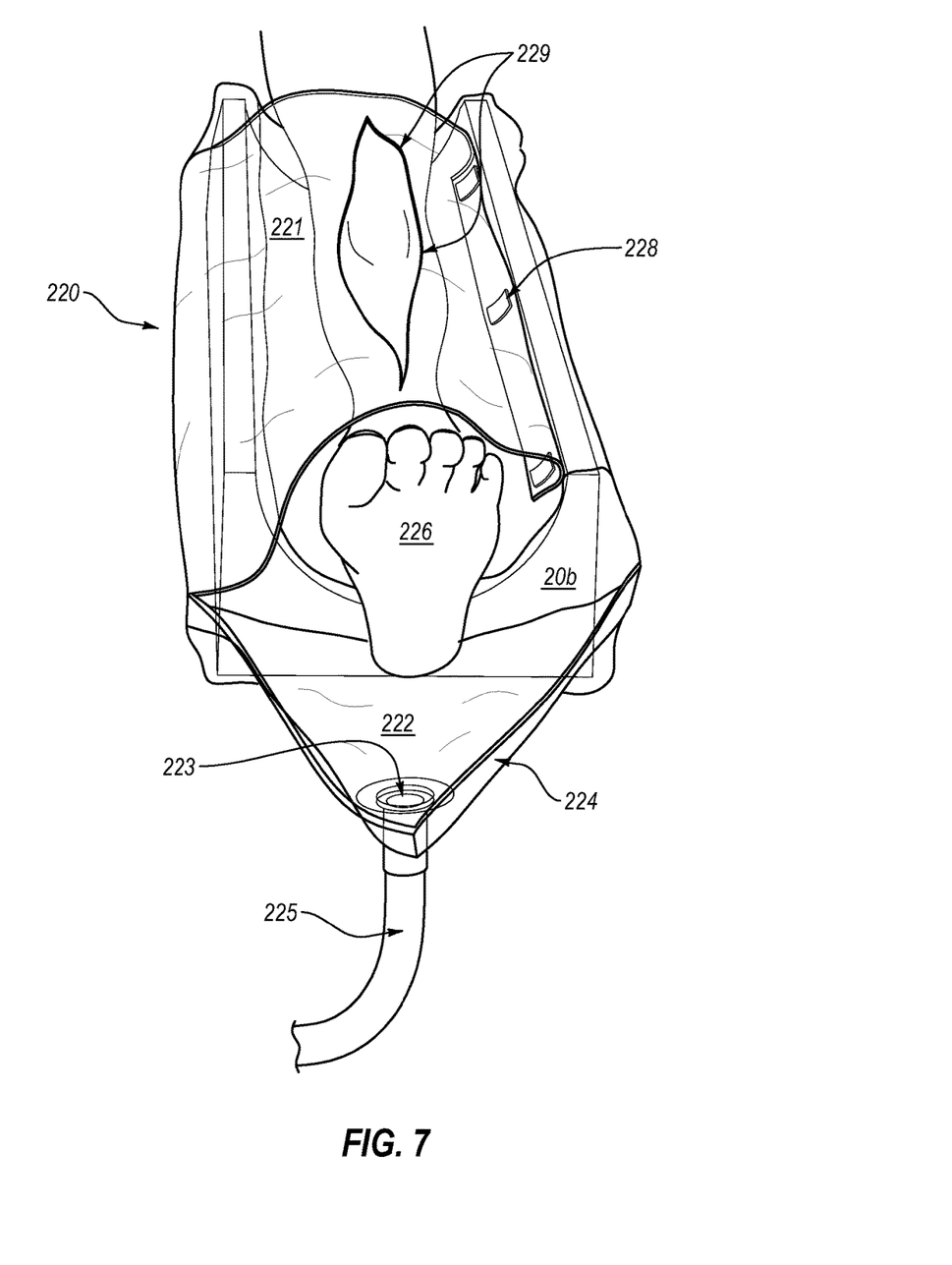
FIG. 7 illustrates the apparatus of FIG. 6 with an opening formed in an upper portion of the barrier shroud to facilitate access by a debridement instrument to the patient extremity (leg).

Shroud 200 may also include one or more slit openings, such as the opening 229 shown in FIG. 7, formed in top portion 201 so as to allow access to patient extremity 206 by a debridement instrument during a debridement procedure. The opening 229 may advantageously be formed by cutting into top portion 201 of shroud 200 by scissors or a scalpel.

Referring now to FIGS. 4-7, another embodiment of an illustrative barrier shroud 220 for use with an extremity-supporting base 20b similar support base 20 is shown. The features of barrier shroud 220 are similar to those of barrier shroud 200 shown in FIG. 3, with three primary exceptions: shroud 220 has no brace 207; shroud 220 is open at both ends, not just at the end associated with the proximal end of the base; and shroud 220 has a separate shroud dam 224 formed into or attached to a bottom portion 222 and does not, as is illustrated in FIG. 3, rely upon the region where the top and bottom portions meet to function as the shroud dam. Otherwise, barrier shroud 220 has a top portion 221, a bottom portion 222 placed over the support surface of base 20b, a shroud drainage opening 223, a shroud dam 224, and a drainage hose 225.

Shroud dam 224 can be a ridge-like structure formed into bottom portion 222 of shroud 220 and may be positioned beyond and below the distal end of the base in close proximity to shroud drainage opening 223 such that fluid and tissue debris associated with debridement may pool in the area near shroud drainage opening 223 and exit shroud drainage opening 223 with the aid of either gravity or applied vacuum suction. Alternatively, shroud dam 224 may be a separately formed structure that is fixedly attached to shroud bottom 222 using known methods, such as heat to the shroud dam 224 to shroud bottom portion 222, or glue, or other adhesives.

As can be seen in FIG. 4, top portion 221 can open and close like a flap, and shroud 220 is open at both ends adjacent the proximal and distal ends of the base. Top portion 221 is permanently joined to bottom portion 222 along one edge of shroud 220 and is releasably attachable to bottom portion 222 along the opposite edge using known fastening devices 228 such as snaps, Velcro®, buttons, hooks, clasps or zippers.

Figure 5:
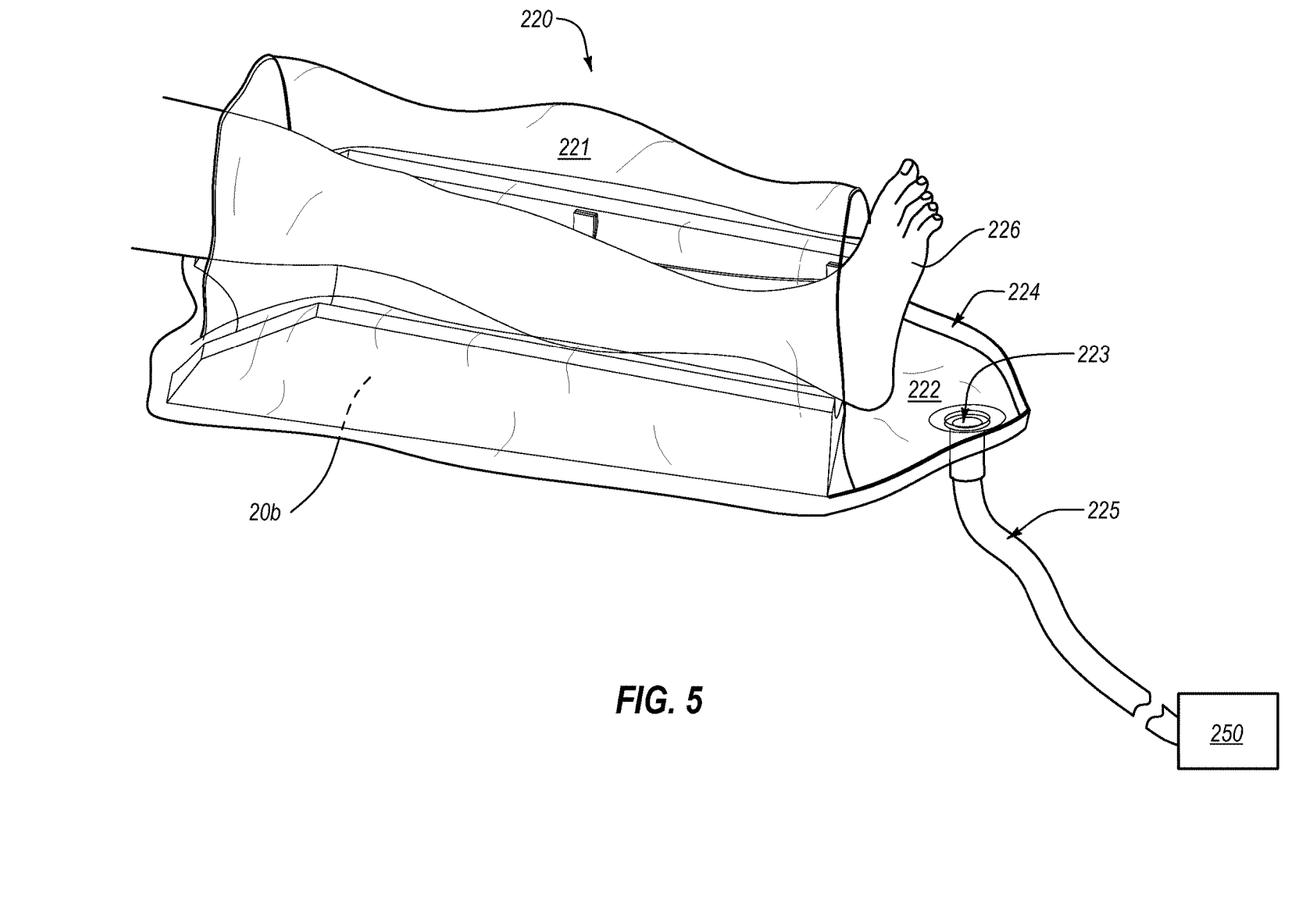
FIG. 5 illustrates the embodiment of FIG. 4 supporting a patient extremity (leg) ready to undergo tissue debridement.
Figure 6:
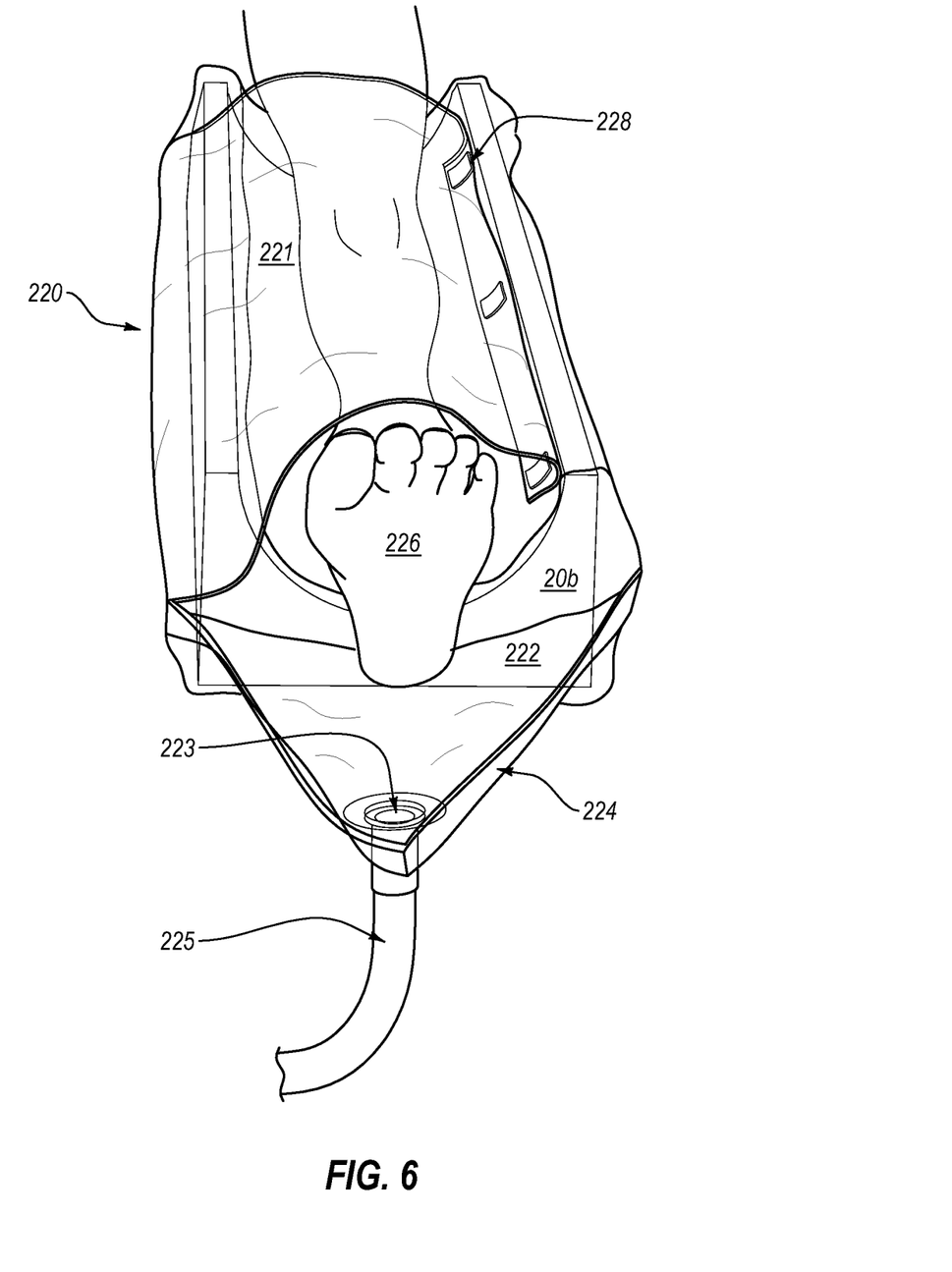
FIG. 6 is an alternative view of the apparatus and leg illustrated in FIG. 5.

As illustrated in FIG. 4, barrier shroud 220 is in a first configuration in which bottom portion 222 (i.e., a first barrier sheet portion) is vertically unobstructed to permit an extremity (e.g., arm or leg) to be lowered from a position above and downwardly onto bottom portion 222 so as to be supported by the support surface of base 20b. As illustrated in FIGS. 5-7, barrier shroud 220 is in a second configuration in which top portion 221 (i.e., a second barrier sheet portion) is positioned over bottom portion 222 and the extremity (leg) in order to at least partially cover the extremity (leg) placed on the first sheet portion and mechanically supported by the support surface of base 20b.

As illustrated in FIGS. 4-7, barrier shroud 220 comprises a transparent, flexible sheet material, such as a polymer sheet material, wherein a first or bottom portion 222 of barrier shroud 220 is positioned over the support surface of base 20b to provide a water-resistant barrier between the support surface and an extremity (e.g., arm or leg) placed thereon and second or top portion 221 of barrier shroud 220 is selectively positionable to provide the first and second configurations of the barrier illustrated in FIGS. 4 and 5-7, respectively.

FIGS. 5-7 show the embodiment of FIG. 4 in use, where the support surface of base 20b and shroud 220 cooperate to support and enclose a patient extremity (leg) 226. FIG. 5 illustrates an aspiration device 250 for applying suction to drainage hose 225. FIG. 6 shows the same configuration of base 20b, extremity 226, and shroud 220, but viewed from the distal end 22 of the base 20b towards the proximal end 21 of the base 20b. FIG. 7 is the same as FIG. 6 but illustrates the incorporation of at least one opening 229, in the form of a slit (or cut) in the embodiment shown, in top portion 221 of shroud 220 so as to allow access to patient extremity 226 by the debridement instrument being operated by the medical personnel.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus for supporting and at least partially enclosing an extremity of a patient during tissue irrigation and debridement, comprising:

a support base extending between a proximal end and a distal end and having a bottom side and a top side providing a concave support surface of continuous contour along an entire length between the proximal end and the distal end for placement and support of an extremity thereon; and a barrier comprising a flexible sheet, the flexible sheet comprising:
  a first barrier portion positioned over the support surface;
  a second barrier portion selectively moveable between an open configuration, in which the first barrier portion positioned over the support surface is vertically unobstructed by the second barrier portion to permit an extremity to be positioned downwardly onto the first barrier portion, and a closed configuration, in which the second barrier portion is positioned over the first barrier portion in order to at least partially cover an extremity when positioned on the first barrier portion and mechanically supported by the support surface; and
  a third barrier portion positioned beneath the bottom side of the support base so that the first and third barrier portions form an enclosure having an open proximal end and a closed distal end and that encloses the support base, including the top and bottom sides of the support base, during use.

2. The apparatus of claim 1, wherein the top side of the support base has a height at the proximal end that is no higher than a maximum height of the support surface and a height at the distal end that is no higher than a minimum height of the support surface, and wherein the support surface slopes downwardly from the proximal end to the distal end to facilitate drainage of irrigation fluid beyond the distal end of the support surface.

3. The apparatus of claim 2, further comprising a drainage hole though a bottom portion of the barrier that is distal to the distal end of the support base and a drainage tube in fluid communication with the drainage hole that are configured to facilitate collection of irrigation fluid and debris during irrigation and debridement.

4. The apparatus of claim 3, further comprising a filter adjacent to or in the drainage hole configured to filter debris from irrigation fluid and prevent or reduce plugging of the drainage tube.

5. The apparatus of claim 1, wherein the support surface is an elongate structure having a length and width adapted to support at least a majority of the length of a human leg or arm when placed thereon.

6. The apparatus of claim 5, wherein the support surface is adapted to support at least a majority of a length of a human leg.

7. The apparatus of claim 5, wherein the support surface is adapted to support at least a majority of a length of a human arm.

8. The apparatus of claim 5, wherein the bottom side of the support base is generally flat and the concave support surface forms a continuous trough of fixed length, fixed width, and fixed depth, and wherein the proximal and distal ends of support base include no wall extending higher than the support surface.

9. The apparatus of claim 5, wherein the barrier comprises a flexible polymer sheet.

10. The apparatus of claim 1, wherein the support base comprises a rigid or semi-rigid material that is non-collapsible so as to have a fixed length from the proximal end to the distal end.

11. The apparatus of claim 1, wherein the support base comprises a cushioning polymer foam material.

12. The apparatus of claim 1, wherein the barrier comprises a material that is more flexible than the support base.

13. The apparatus of claim 1, wherein the barrier comprises one or more fasteners that selectively fasten or unfasten so that the second barrier portion is selectively unfastened when in the open configuration and selectively fastened to maintain the second barrier portion in the closed configuration.

14. The apparatus of claim 1,
the barrier further comprising:
  a distal bottom portion extending distally beyond the distal end of the support base;
  a drainage opening in said distal bottom portion and positioned distally beyond the distal end of the support base; and
  a dam positioned distal to the drainage opening,
    wherein the distal bottom portion, the drainage opening, and the dam cooperate to collect fluid and tissue debris that flow distally beyond the distal end of the support base.

15. An apparatus for supporting and at least partially enclosing an extremity of a patient during tissue irrigation, comprising:
  a support base comprising a rigid or semi-rigid material extending between a proximal end and a distal end and having a bottom side and a top side providing a support surface of fixed longitudinal length for placement and mechanical support of an extremity thereon; and
  a barrier comprising a flexible sheet, the flexible sheet comprising:
    a first sheet portion positioned on the support surface;
    a second sheet portion selectively positionable between a first configuration, in which the first sheet portion is vertically unobstructed to permit an extremity to be positioned downwardly onto the first sheet portion, and a second configuration, in which the second sheet portion is positioned over the first sheet portion in order to at least partially cover an extremity when positioned on the first sheet portion and mechanically supported by the support surface; and
    a third sheet portion positioned beneath the bottom side of the support base so that the first and third sheet portions form a bag or sleeve structure having an open proximal end and a closed distal end and that encloses the support base, including the top and bottom sides of the support base, during use.

16. The apparatus of claim 15, wherein the support base has a maximum height at the proximal end that is no greater than a maximum height of the support surface and a maximum height at the distal end that no greater than a minimum height of the support surface at the distal end, and wherein the support surface slopes downwardly and facilitates drainage of irrigation fluid beyond the distal end of the support base.

17. The apparatus of claim 16, wherein the top side of the support base is concave so that the support surface provides a downwardly sloping trough of fixed length, fixed width, and fixed depth.

18. The apparatus of claim 15, further comprising one or more fasteners that selectively fasten or unfasten so that the second sheet portion is selectively unfastened when in the first configuration and selectively fastenable to maintain the second sheet portion in the second configuration.

* * * * *

UNITED STATES PATENT AND TRADEMARK OFFICE
CERTIFICATE OF CORRECTION

| | | |
|---|---|---|
| PATENT NO. | : 10,278,878 B2 | Page 1 of 1 |
| APPLICATION NO. | : 15/626469 | |
| DATED | : May 7, 2019 | |
| INVENTOR(S) | : Parsell et al. | |

It is certified that error appears in the above-identified patent and that said Letters Patent is hereby corrected as shown below:

In the Specification

Column 4
Line 41, delete "or"
Line 43, change "distal so" to –distal end so–

Column 5
Line 55, change "the and weight" to –and the weight–

Column 8
Line 29, change "cooperate" to –cooperates–

Signed and Sealed this
Twenty-first Day of April, 2020

Andrei Iancu
*Director of the United States Patent and Trademark Office*